US00RE34353E

United States Patent [19]

Perry et al.

[11] E Patent Number: Re. 34,353

[45] Reissued Date of Patent: Aug. 24, 1993

[54] TOUCH ENHANCING PAD

[75] Inventors: Don A. Perry; H. Earl Wright, both of Decatur, Ill.

[73] Assignee: Inventive Products, Inc., Decatur, Ill.

[21] Appl. No.: 337,253

[22] Filed: Apr. 13, 1989

Related U.S. Patent Documents

Reissue of:

[64] Patent No.: 4,657,021
Issued: Apr. 14, 1987
Appl. No.: 726,767
Filed: Apr. 24, 1985

[51] Int. Cl.[5] ..... A61B 19/00

[52] U.S. Cl. ..... 128/630; 604/346; 383/118; 434/267

[58] Field of Search ..... 128/846, 630, 774; 2/168, DIG. 7; 383/3, 116, 118; 434/267, 272, 273; 604/346, 349

[56] References Cited

U.S. PATENT DOCUMENTS 1,169,804 2/1916 Gregory ..... 383/3
2,326,159 8/1943 Mendel ..... 604/349
2,694,396 11/1954 Paschal ..... 128/67
3,136,417 6/1964 Clinch ..... 604/349
3,149,017 9/1964 Ehrreich ..... 383/3
4,143,423 3/1979 Sternlieb ..... 604/349

FOREIGN PATENT DOCUMENTS 645391 5/1937 Fed. Rep. of Germany .

OTHER PUBLICATIONS

Madden; Journal of Bioengineering; vol. 2, pp. 427–435, 1978.

*Primary Examiner*—Randy C. Shay
*Attorney, Agent, or Firm*—Philip L. Bateman

[57] ABSTRACT

An apparatus enhances the sense of touch when placed between the fingertips of the user and the object being touched. The apparatus comprises a liquid lubricant inside a sealed enclosure. The enclosure is formed of a pliable, elastic material having a wall thickness of about 0.005 to 0.020 inches. The liquid lubricant is present in an amount sufficient to fully coat the interior of the enclosure, but which also permits the enclosure to be flattened with at least about 75 percent of the surface area of one side in contact with the other side.

12 Claims, 2 Drawing Sheets

TOUCH ENHANCING PAD

Matter enclosed in heavy brackets [ ] appears in the original patent but forms no part of this reissue specification; matter printed in italics indicates the additions made by reissue.

FIELD OF THE INVENTION

This invention relates to an apparatus which enhances the sense of touch.

BACKGROUND OF THE INVENTION

The sense of touch is one of the five senses by which we gather information about the world around us. The sense of touch gives rise to feelings of pleasure and pain and is used to determine the shape, hardness, texture, and temperature of objects. The sense of touch is used extensively in the field of medicine because the shape and hardness of body internals is often an excellent guide in diagnosing and treating disease.

One of the most publicized uses of the sense of touch in medical diagnosis is the detection of breast cancer. One out of every eleven women in the United States develops breast cancer. It is the most common form of cancer in woman and is the chief cause of cancer deaths among United States women. Early detection of breast cancer is considered extremely important in treating the disease. Breast cancer is characterized by the formation of lumps in the breast. These lumps can be detected by X-ray radiation photography or by manual examination. The known tendency of X-ray radiation to cause various types of cancer generally prevents its routine use for detection. Accordingly, most breast cancers are discovered by the detection of lumps by physical examination of the breasts. Manual examination of the breasts is included by most physicians in their routine examinations of adult women. To help with early detection, the American Cancer Society also recommends monthly self-examinations for women.

To reduce friction and thereby facilitate movement of the hands across the breasts, the American Cancer Society recommends that the monthly self-examinations be conducted during a bath or shower when the skin is wet and soapy. For any number of reasons, many women find it inconvenient to take the additional time for self-examination during their bath or shower. And, for obvious reasons, it is not practical to use water and/or soap as a skin lubricant for breast examination when partially clothed, e.g., at a physician's office. Creams, powders, or lotions are more suitable as friction reducers, but still are rarely used because of the mess. Therefore, most physicians and women conduct breast examinations by using their hands directly on dry skin.

Unfortunately, manual examination of the breasts does not ensure that a lump will be detected. In an article entitled "Physicians' Abilities to Detect Lumps in Silicone Breast Models" published in the Apr. 19, 1985 issue of the Journal of The American Cancer Society, (Vol. 253, No. 15, pp. 2224–2228) Dr. Suzanne W. Fletcher et al. of the University of North Carolina at Chapel Hill described a study which tested the ability of 80 physicians to detect lumps of varying sizes, hardness, and depth in silicone breast models. Dr. Fletcher et al. found that the physicians were able to detect only 44 percent of the lumps.

It is not difficult to understand why the detection results were so poor in the study. When conducting a breast cancer examination with bare hands on dry skin, the examiner must ignore the unwanted touch stimuli (i.e., the "noise", e.g., temperature, texture, and, if a self-examination, stimuli from the breast itself) in favor of the desired touch stimuli which enable the determination of shape and hardness of an object (i.e., the "signal"). The sense of touch is clearly an ability which can be developed with practice. For example, thousands of blind persons are able to "read" braille lettering, but a sighted person touching braille for the first time is usually unable to distinguish the number or pattern of the protrusions. Consequently, Dr. Fletcher et al. recommended more training for physicians to better develop their senses of touch.

Paschal, U.S. Pat. No. 2,694,396, issued Nov. 16, 1954, discloses and claims a massaging pad formed by sewing together a pair of satin sheets in such a way that friction between the sheets is reduced (the "warp" of one sheet is disposed at a substantial angle to the "warp" of the other). Paschal also discloses a modified form of the device comprising two sheets of flexible plastic material fused or sealed together with a lubricant on the inside. The Paschal device is allegedly an aid to massagers because it reduces the friction between the massager's hands and the body part being massaged. The device does not, however, enhance the sense of touch. Instead, the device masks the sense of touch because it is made of materials which do not readily transmit touch stimuli.

SUMMARY OF THE INVENTION

The general object of this invention is to provide an apparatus which enhances the sense of touch. A more particular object is to provide an apparatus which improves the ability to detect breast cancer by physical examination.

We have discovered an apparatus which enhances the sense of touch when placed between the fingertips of the user and the object being touched. The apparatus comprises: (a) a sealed enclosure of a pliable, elastic material having a wall thickness of about 0.005 to 0.020 inches, a modulus at 300 percent of less than about 1,500 lbs/sq. in. ("psi"), a tensile strength of greater than about 3,000 psi, and an ultimate elongation of greater than about 400 percent; and (b) a liquid lubricant inside the enclosure which has sufficient lubricity to reduce the coefficient of kinetic friction between the interior walls of the enclosure by at least about 60 percent, a sufficiently-high resistance to mass transfer through the enclosure so that the amount of lubricant inside the enclosure remains substantially constant over time, substantial inertness towards the enclosure, and which is present in an amount sufficient to fully coat the interior of the enclosure, provided that the amount of the liquid lubricant permit the enclosure to be flattened with at least about 75 percent of the surface area of one side in contact with the other side.

The use of this apparatus enhances the sense of touch and thereby improves the ability of its user to detect breast cancer by physical examination. The apparatus is also useful in other applications where the sense of touch is employed for diagnosis. The apparatus is non-toxic, reuseable, and leaves no residue on the hands of the user or on the object being touched.

DETAILED DESCRIPTION OF THE INVENTION

Figure 1:
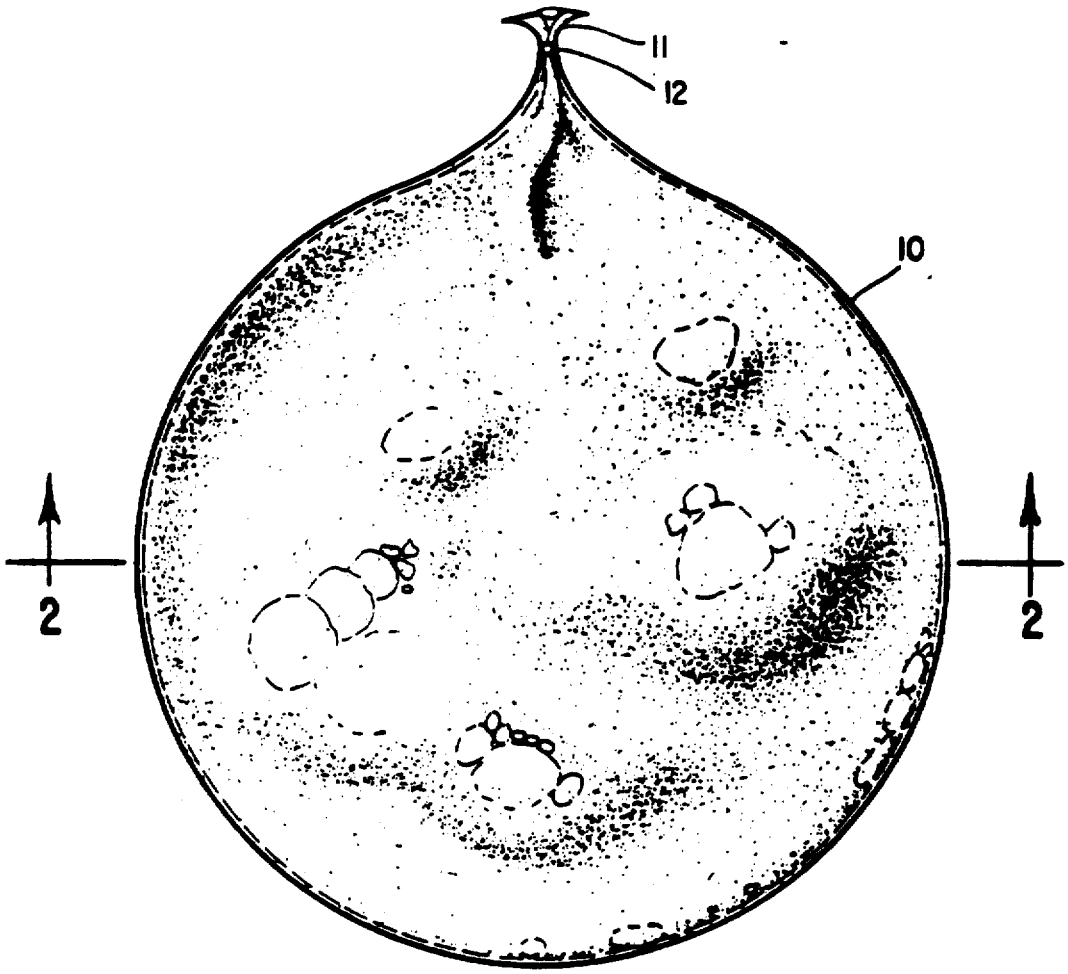
FIG. 1 is a top view *of one embodiment* of the apparatus.
Figure 2:
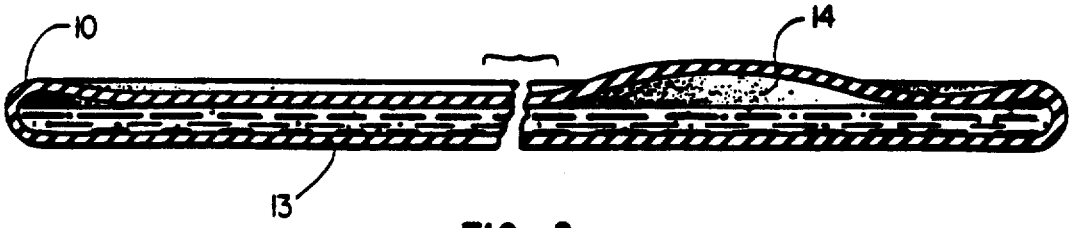
FIG. 2 is a cross-sectional view of the *embodiment of FIG. 1 of the* apparatus.

This invention is best understood by reference to the drawings. FIG. 1 is a top view of the touch enhancing pad showing an enclosure 10 which has an opening 11 closed off with a physical seal 12. FIG. 2 is a cross-sectional view of the pad showing a quantity of a liquid lubricant 13 and a gas 14 inside the pad. To use the pad, it is first placed onto the object to be touched. The fingertips are then used to examine the object just as if the pad were not present. The bottom wall of the pad (the one in contact with the object being touched) generally remains stationary while the top wall (the one in contact with the fingertips) moves with the fingertips. For what is believed to be a number of reasons, the touch stimuli used to determine shape and hardness are enhanced when the pad is used in this fashion.

The enclosure is made of a material which readily transmits the desired touch stimuli through two of its layers and yet is strong enough to resist tearing or puncturing. The ability of a material to transmit touch stimuli is believed to be primarily a function of its thickness and its ability to conform to the contours of the object being touched. This ability to conform is, in turn, primarily a function of the material's pliability and elasticity. In summary, the properties desired for the enclosure material are strength, pliability, and elasticity.

The material preferably has a tensile strength of greater than about 3,000 psi and most preferably greater than about 4,000 psi. The material has a thickness of about 0.005 to 0.020 inches. At this thickness, and with a tensile strength of greater than about 3,000 psi, the material is strong enough to resist tearing or puncturing and yet thin enough to readily transmit touch stimuli. The material preferably has a thickness of about 0.010 to 0.015 inches.

The pliability of a material can be measured in terms of its modulus. Modulus is the force required to stretch a material a given amount. For use in this invention, a material preferably has a modulus at 300 percent of less than about 1,500 psi and most preferably less than about 700 psi.

The material preferably has sufficient elasticity so that it can be stretched to at least four times its length without breaking. In other words, it is preferred that the material have an ultimate elongation of greater than 400 percent. It is most preferred that the ultimate elongation exceed 600 percent.

Figure 3:
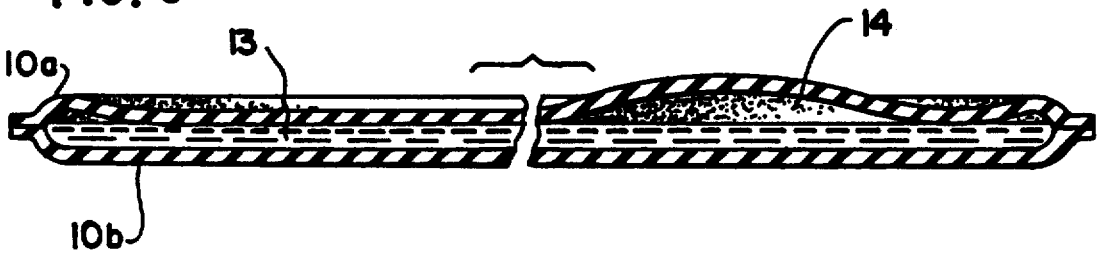
*FIG. 3 is a cross-sectional view of a second embodiment of the apparatus.*

Although a plurality of pieces of material, *as shown as pieces 10a and 10b in FIG. 3* can be joined together to form the enclosure, it is preferred that the enclosure be formed of a single piece of material because the presence of a seam of any type tends to interfere with the movement of the pad during use. The enclosure may be of any desired shape or size. For breast examination, a round enclosure having a diameter of about 9 inches is preferred because it fully covers the breast. A highly preferred enclosure has the general shape of a round toy balloon with the single opening physically sealed to prevent the flow of liquid or gas therethrough. Suitable physical seals are clamps, bands, and the like. The interior walls of the enclosure are preferably as smooth as possible to facilitate low-friction movement of one side against the other.

Materials exhibiting the above-described properties of strength, pliability, and elasticity are generally members of the class of polymers known as rubbers. A rubber enclosure of the preferred shape and wall thickness is conveniently manufactured by a process known as "dipping". In this process, a suitably-shaped metal or ceramic paddle is dipped into an emulsion of rubber polymer in water known as latex. The latex generally contains a vulcanizing ingredient, such as sulfur, and may also contain a coagulant to improve the deposition of rubber upon the paddle. After the desired period of dipping (ranging from seconds to several minutes), the paddle is withdrawn and dried. The dry, vulcanized rubber product is then removed from the paddle. This method of manufacture is widely used for producing surgeons gloves, toy balloons, etc.

Both synthetic and natural rubber latexes are suitable for use in making the enclosure. Synthetic rubber latexes are made of many different polymers, including polychloroprene, butadiene-styrene copolymer, butadiene-acrylonitrile copolymer, etc. Natural rubber latex is obtained from the tree Hevea Braziliensis and is cleaned, preserved, and concentrated before use. The natural rubber latex is preferred because dipped rubber products from it generally exhibit superior properties of strength, pliability, and elasticity.

The liquid lubricant reduces the friction between the interior walls of the enclosure and thereby eases movement of the top wall across the stationary bottom wall. The lubricant has sufficient lubricity to reduce the coefficient of kinetic friction between the interior walls by at least about 60 percent. The lubricant also has a sufficiently-high resistance to mass transfer through the walls of the enclosure so that the amount of lubricant inside the enclosure remains substantially constant over time. A mixture of water and soap is inexpensive, nontoxic, and has sufficient lubricity, but water tends to permeate through thin rubber walls, especially at elevated temperatures. The lubricant further has substantial inertness towards the enclosure so that it does not cause failure of the enclosure. Petroleum fractions and animal and vegetable oils are generally unsatisfactory due to their effect on rubber, especially natural rubber latex.

The liquid lubricant is present in an amount large enough to fully coat the interior of the enclosure and yet small enough so that the user of the pad can examine an object with only a minimum layer of lubricant between the walls of the enclosure. The amount of the liquid lubricant preferably permits the enclosure to be flattened with at least about 75 percent of the surface area of one side in contact with the other side. As an example, about 10 to 30 ml of lubricant are preferred for use with a 9 inch diameter pad. While not critical to the invention, it is, of course, preferred that the lubricant be non-toxic. Preferred liquid lubricants include glycerine, propylene glycol, and polyoxyethylene (also known as polyethylene glycol). Propylene glycol is the most preferred lubricant.

The ease with which the pad is used is improved somewhat if a volume of gas is also present inside the enclosure. The gas has substantial inertness towards the enclosure and is preferably air because of ease of manufacture. The volume of the gas is generally at least about double the volume of the liquid lubricant. The combined volumes of the liquid lubricant and the gas permit the enclosure to be flattened with at least about 75 percent of the surface area of one side in contact with the other side. In the example of the 9 inch diameter pad, about 100 to 500 ml of gas are preferred.

While not wishing to be bound by theory, it is believed that at least five factors contribute to the touch enhancing properties of the pad of this invention. First of all, the pad eliminates or masks certain touch stimuli such as temperature and texture and thereby improves the ability to detect the touch stimuli which enable the determination of shape and hardness. Secondly, the pad reduces friction between the user and the object being touched. This eases the movement of the fingertips across the object and helps prevent any tendency of the fingertips to skip across a portion of the object.

Thirdly, the pad helps immobilize the object being touched. A very small object, protrusion, or indentation is detected most readily by passing the fingertips across it. If the object moves with the fingertips, it is more difficult to detect. For example, it is very difficult to feel a single human hair upon a hard, smooth surface. At least part of the difficulty is because the hair tends to stick to the fingers. When the pad is used, the hair is immobilized and the fingertips can be moved back and forth across the hair, enabling it to be detected.

Fourthly, the pad adheres to and follows the contours of objects so well that it, in effect, increases the size of the object for detection purposes. In the above example of the human hair, the increase in the hair's diameter by several thousandths of an inch (which results when one wall of the enclosure adheres to the hair) creates a much larger protrusion for the fingertips to feel. Fifthly, the pad may actually increase the surface area of the fingertips in contact with an object.

We claim:

1. An apparatus which enhances the sense of touch when placed between the fingertips of the user and the object being touched, the apparatus comprising:

(a) a sealed enclosure of a single piece of a pliable, elastic material having a wall thickness of about 0.005 to 0.020 inches, a modulus at 300 percent elongation of less than about 1,500 psi, a tensile strength of greater than about 3,000 psi, and an ultimate elongation of greater than about 400 percent so that the enclosure is resistant to tearing or puncturing and is able to conform to the contours of the object being touched and to readily transmit touch stimuli; and (b) a liquid lubricant inside the enclosure which has sufficient lubricity to reduce the coefficient of kinetic friction between the interior walls of the enclosure by at least about 60 percent so that the bottom wall of the pad remains stationary over the object being touched while the top wall moves freely with the fingertips, a sufficiently-high resistance to mass transfer through the enclosure so that the amount of lubricant inside the enclosure remains substantially constant over time, substantial inertness towards the enclosure, and which is present in an amount sufficient to fully coat the interior of the enclosure, provided that the amount of the liquid lubricant permits the enclosure to be flattened with at least about 75 percent of the surface area of one wall in contact with the other wall with only a minimum layer of lubricant between the walls.

2. The apparatus of claim 1 wherein the enclosure comprises rubber prepared from natural or synthetic rubber latex.

3. The apparatus of claim 2 additionally comprising a gas inside the enclosure which has substantial inertness towards the enclosure and which is present in a volume at least about double the volume of the liquid lubricant, provided that the combined volumes of the liquid lubricant and the gas permit the enclosure to be flattened with at least about 75 percent of the surface area of one side in contact with the other side.

4. The apparatus of claim 3 wherein the enclosure is formed of a single piece of rubber which has a single opening physically sealed to prevent the flow of liquid or gas therethrough.

5. The apparatus of claim 4 wherein the gas comprises air.

6. The apparatus of claim 5 wherein the enclosure comprises rubber prepared from natural rubber latex.

7. The apparatus of claim 6 wherein the enclosure material has a modulus of 300 percent of less than about 700 psi, a tensile strength of greater than about 4,000 psi, and an ultimate elongation of greater than about 600 percent.

8. The apparatus of claim 7 wherein the lubricant comprises glycerine, polyethylene glycol, or propylene glycol.

9. The apparatus of claim 8 wherein the enclosure has a wall thickness of about 0.010 to 0.015 inches.

10. The apparatus of claim 9 wherein the lubricant comprises propylene glycol.

11. A method of enhancing the sense of touch which comprises placing the apparatus of claim 1, 2, 3, 4, 5, 6, 7, 8, 9, or 10 between the fingertips of the user and the object being touched.

*12. An apparatus which enchances the sense of touch when placed between the fingertips of the user and the object being touched, the apparatus comprising:*

*(a) a sealed enclosure of a plurality of pieces of a pliable, elastic material having a wall thickness of about 0.005 to 0.00 inches, a modulus of 300 percent elongation of less than about 1,500 psi, a tensile strength of greater than about 3,000 psi, and an ultimate elongation of greater than about 400 percent so that the enclosure is resistant to tearing or puncturing and which is adapted to conform to the contours of the object being touched and to readily transmit touch stimuli; and*

*(b) a liquid lubricant inside the enclosure which has sufficient lubricity to reduce the coefficient of kinetic friction between the interior walls of the enclosure by at least about 60 percent so that the bottom wall of the pad remains stationary over the object being touched while the top wall moves freely with the fingertips, a sufficiently-high resistance to mass transfer through the enclosure so that the amount of lubricant inside the enclosure remains substantially constant over time, substantial inertness towards the enclosure, and which is present in an amount sufficient to fully coat the interior of the enclosure, provided that the amount of the liquid lubricant permits the enclosure to be flattened with at least about 75 percent of the surface area of one wall in contact with the other wall with only a minimum layer of lubricant between the walls.*

* * * * *

UNITED STATES PATENT AND TRADEMARK OFFICE

CERTIFICATE OF CORRECTION

PATENT NO. : Re. 34,353

DATED : August 24, 1993

INVENTOR(S) : Don A. Perry, et al

It is certified that error appears in the above-indentified patent and that said Letters Patent is hereby corrected as shown below:

Column 6, lines 43-44, "0.005 to 0.00 inches" should read --0.005 to 0.020 inches--

Signed and Sealed this

Thirtieth Day of August, 1994

*Attest:*

*Attesting Officer*

BRUCE LEHMAN

*Commissioner of Patents and Trademarks*